United States Patent [19]

Osgood

[11] Patent Number: 5,712,084
[45] Date of Patent: Jan. 27, 1998

[54] DONOR KIDNEY VIABILITY TEST FOR IMPROVED PRESERVATION

[75] Inventor: Richard W. Osgood, North Riverside, Ill.

[73] Assignee: Research Corporation Technologies, Inc., Tucson, Ariz.

[21] Appl. No.: 526,121

[22] Filed: Sep. 8, 1995

[51] Int. Cl.$^6$ .................................................. A01N 1/02
[52] U.S. Cl. .................................................. 435/1.2; 435/4
[58] Field of Search .................................. 435/1.2, 4

[56] References Cited

U.S. PATENT DOCUMENTS

| | | | |
|---|---|---|---|
| 4,798,824 | 1/1989 | Belzer et al. | 514/60 |
| 4,873,230 | 10/1989 | Belzer et al. | 514/60 |

OTHER PUBLICATIONS

Meguro J, Nippon Geka Gakkai Zasshi. J. Japan Sur. Soc. 95(6) 400–10 (1994).
Derwent WPI Online Abstract Accession No. 80–12360C (Jun. 5, 1979), SU 665916.
Derwent WPI Online Abstract Accession No. 90–146486 (Jul. 30, 1989), SU 1496740.
Abstract No. 72409 (1975) "Tubular Water Reabsorption as a Viability Indicator in the Preserved Canine Kidney", *Biological Abstracts* 63, Michels et al., Transplantation 22(5):522–26 (1976).
Abstract No. 25754 (1978) "An Intermittent Urinary Flow Method of Assessing Viability in Warm Ischemic Kidneys During 48 to 96 Hours of Perfusion", *Biological Abstracts* 67, Proctor et al., Transplantation 25(5):280–81 (1978).
Abstract No. 109223 (1988) "Successful 72–Hour Cold Storage of Dog Kidneys with UW Solution", *Biological Abstracts* 86, Ploeg et al., Transplantation 46(2):191–6 (1988).
D'Alessandro et al. (Oct., 1994) "Organ Preservation" in Horizons in Organ Transplantation *Surgical Clinics Of North America* 74: 1083–1095.
Gianello et al. (1994) "Measuremet of the vasoconstrictive substances endothelin, angiotensin II, and thromboxane B, in cold storage solution can reveal previous renal ischemic insults" *Springer–verlag Transpl Int* 7:11–16.
Lloveras et al "Optimization of In Situ Renal Perfusion of Non–Heart Beating Donors: Four–Lumen Catheter Developed for Continuous Perfusion Pressure Determination" *Transplantation Proceedings* 25 (6): 3169–3170 (1993).
Gnant et al. (Dec. 1993) "Impact of Donor Cause of Death on Renal Graft Function—A Multivariate Analysis of 1545 Kidney Transplants" *Transplantation Proceedings* 25 (6): 3102–3103.
Rowinski et al. (Feb. 1993) "Use of Kidneys From Marginal and Non–Heart Beating Donors: Warm Ischemia Per Se Is Not The Most Detrimental Factor" *Transplantation Proceedings* 25 (1): 1511–1512.
Booster et al. (Feb. 1993) "In Situ Perfusion of Kidneys From Non–Heart Beating Donors: The Maastricht Protocol" *Transplantation Proceedings* 25 (1): 1503–1504.
Marshall et al. (Feb. 1991) "University of Wisconsin Solution For Kidney Preservation: The Impermeant Components" *Transplantation Proceedings* 23 (1): 651–652.

Merkus, et al. (1991) "Detrimental Effect of Aacute Renal Failure on the Survival of Renal Allografts: Influence of Total Ischaemia Time and Anastomosis Time" *Neprhol Dial Transplant* 6: 881–886.
Southard et al. (1990) "Important Components Of The UW Solution" *Transplantation* 49 (2): 251–257.
Johnson et al. (Apr. 1990) "Local Procurement with Pulsatile Perfusion Give Excellent Results and Minimizes Initial Cost Associated with Renal Transplantation" *Transplantation Proceedings* 22 (2): 385–387.
Belzer et al. (Feb. 1989) "Combined Cold Storage–Perfusion Preservation of the Kidney with a New Synthetic Perfusate" *Transplantation Proceedings* 21 (1): 1240–1241.
Hoffmann et al. (Jan. 1989) "Combined Cold Storage–Perfusion Preservation With A New Synthetic Perfusate" *Transplantation* 47 (1): 32–37.
Southard, J.H. (1989) "Viability Assays in Organ Preservation" *Cryobiology* 26:232–238.
Belzer et al. (Apr. 1988) "Principles of Solid–Organ Preservation By Cold Storage" *Transplantation* 45 (4): 673–676.
Zager, R.A. (Oct. 1987) "Partial aortic ligation: A hypoperfusion model of ischemic acute renal failure and a comparison with renal artery occlusion" *J. Lab. Clin. Med.* 110 (4): 396–405.
Southard et al. (1985) "Long Term Kidney Preservation on Glomerular Ultrastructure" *Cryobiology* 22: 615.
Southard et al. (1985) "Effects of Short–Term Hypothermic Perfusion and Cold Storage on Function of the Isolated–Perfused Dog Kidney" *Cryobiology* 22: 147–155.
Hoffmann et al. (Oct. 1988) "Efficacy of Clinical Cadaver Kidney Preservaton by Continuous Perfusion" *Transplantation Proceedings* XX (5): 882–884.
Hoffmann et al. (Aug. 1983) "Synthetic Perfusate for Kidney Preservation Its Use in 72–Hour Preservation of Dog Kidneys" *Arch Surg* 118: 919–921.
Belzer et al. (Mar. 1982) "A New Perfusate For Kidney Preservation" *Transplantation* 33 (3): 322–323.
Hoffmann et al. (1982) "The use of oncotic support agents in perfusion preservation" in *Organ Preservation Basic and Applied Aspects* MTP Press, Lancaster England 261–265.

*Primary Examiner*—Sandra E. Saucier
*Attorney, Agent, or Firm*—Scully, Scott, Murphy & Presser

[57] ABSTRACT

The present invention contemplates a methodology which employs cold perfusion of donor organs with a colloid preservation solution at a selected perfusion pressure which avoids tubular reabsorption and consequent energy loss. The present invention is also directed towards the direct continuous measurement of Glomerular Filtration Rate (GFR) through measurement of urine formation during the perfusion period. The present invention further provides a method to assess afferent arteriole and efferent arteriole vascular patency. The present invention further contemplates the maintenance of tubular patency during perfusion. The present invention is also directed to a method for monitoring cold ischemia damage as an indication for timing and dosage of nephrotoxic immunosuppressant agents, e.g., Cyclosporin A. The present invention still further contemplates a device for performing the test of the present invention.

8 Claims, 5 Drawing Sheets

DONOR KIDNEY VIABILITY TEST FOR IMPROVED PRESERVATION

FIELD OF THE INVENTION

The present invention relates to the monitoring of donor kidneys to establish their functional state. The diagnostic method of the present invention monitors physiological events during cold storage that can be used to evaluate kidney functionality at harvest, throughout the storage period and just prior to transplantation.

BACKGROUND OF THE INVENTION

Today, seventy-five percent (75%) of all kidney transplants performed in the United States utilize cadaveric organs. The use of cadaveric kidneys requires cold preservation of the organ during donor-recipient preparation. The amount of storage, or cold ischemia time, influences graft survival rates for many years post transplant. Cold ischemia damage is also known to exacerbate Cyclosporin A nephrotoxicity. Thus, Cyclosporin A may cause complications that will threaten graft survival if administered to an ischemically damaged kidney. Current research suggests that the success rate of a transplanted organ is enhanced by a shortened ischemia time (Merkus et al. *Nephrol. Dial. Transplant*, 6:881–886, 1991). The hemodynamic stability of the donor, harvest procedure, preservation procedure, and recipient integrity are other factors influencing transplant outcomes (Gnant et al. *Transpl. Proc.*, 25(6):3102–3103, 1993).

Perfusion of donor kidneys has been proposed to enhance kidney transplant success rates. Research demonstrates that perfusion provides advantages in cost, microvascular preservation and graft function over cold storage (Johnson et al. *Transpl. Proc.* 22(2): 385–387, 1990, Belzer et al. *Transpl. Proc.*, 21(1):1240–1241 1989). However, due to the characteristic difficulty of perfusion and the lack of long-term data on its benefits, most kidney transplant centers currently utilize cold storage preservation.

Additional reluctance to utilize perfusion techniques to preserve donor kidneys is based on ineffective preservation solutions. Conventional perfusates are generally albumin based. Some researchers suggest that albumin may be a limiting factor in the quality and duration of kidney preservation due to substantial metabolic tubular function during cold storage (Hoffmann et al. *Transpl.*, 47(1):32–37, 1989). Albumin also tends to denature over time, causing tissue damage (Hoffmann et al. *Arch. Surg.*, 118:919–921, 1983).

The presence of an impermeable colloid, e.g., albumin in a perfusate is essential however to maintain glomerular integrity, prevent cellular edema and to maintain viability of kidneys during perfusion (Hoffmann et al. supra, 1983). The colloid constituency exerts colloid osmotic pressure. Colloid osmotic pressure in the plasma opposes filtration from the blood vessels so that the perfusate is not forced from the blood vessels into the intercellular spaces of the kidney by the pressure needed for perfusion. Expansion of the intercellular volume due to perfusate filtration causes compression of the kidney vasculature which causes problems in reperfusion after the kidney is transplanted.

As previously indicated, albumin has proved to be an unreliable colloid component in perfusion solutions, particularly since albumin based perfusates have been characterized by substantial metabolic tubular function during cold storage of rat kidneys (Gianello et al. Transpl. Int., 7:11–16, 1994). The metabolic tubular function, documented by inulin analysis to determine filtration rate, includes concurrent reabsorption of sodium and water. Inulin analysis generally involves a multistep, labor and time intensive task of measuring inulin concentrations in blood plasma and urine to generate GFR. Reabsorption uses energy in the form of ATP. It is art accepted that the less energy utilization by stored kidneys, the longer the organs will maintain functionality.

In contrast with albumin based perfusates, a preferable solution currently in the possession of the art is known as the "UW" (University of Wisconsin) solution. The UW solution comprises a mixture of salts, ions, osmotically active materials and colloids. The colloid in the UW solution is modified hydroxyethyl starch (HES) employed at a standard concentration of 5.0 g % (Belzer et al., *Transplant*, 45 (4): 673–676, 1988). The UW solution, as commonly used, is so constituted that it minimizes swelling of blood vessels by proper balance of osmotically active cell membrane permeable and impermeant salts and sugars. Several articles and patents describe using the colloid HES in kidney perfusion solutions. One such patent is U.S. Pat. No. 4,879,283 to Belzer et al. Belzer et al. describe a solution for preserving and storing organs intended for transplantation containing 3.0 g % to 8.0 g % by weight of hydroxyethyl starch.

Current methods of determining the viability of donor organs both pre- and post-transplantation are described in various scientific publications. For example, kidney tissue biopsy is performed before transplantation in patients who have a history of renal disease.

Electrolytes, plasma creatinine, sodium, potassium, ATPase, kidney tissue biopsies, lysosomal enzymes and blood flow have all been used before and/or after transplantation to test organ quality. While some of these tests have been effective in limited circumstances, none has enjoyed widespread acceptance or success.

Despite available techniques to measure the various related parameters, few methods are presently available to assess the continuing functional viability of a donor kidney prior to transplantation. Total (organ) Flow (TF), for example, provides only a general measure of a kidneys functionality. TF is the total fluid flow through the kidneys, generally quantitated in µl/min in rodents and in ml/min in humans. The only method presently available to assess the viability of a donor organ prior to transplantation employs a determination of whether Total Flow (TF) is maintained throughout the vasculature of the kidney. Total organ flow can predict total organ resistance which has some use as a non-specific indicator of organ viability. Total organ resistance provides a general indication of the patency of the kidney vasculature, e.g., as a kidney fails, the vasculature tends to be obstructed as a consequence of cellular swelling or edema. However, total organ flow cannot be used to assess tubule patency or to determine those segments of the kidney vasculature which are changing due to failing functionality. Nor can TF alone be used to evaluate the consequences of those changes, e.g. TF cannot differentiate afferent or efferent arteriole or tubular resistance.

Instead, Glomerular Filtration Rate (GFR) has been used as the measure of kidney function. The consensus for using GFR as the "gold standard" for evaluating the success of transplanted kidney function has long been established. However, continuous filtration testing, i.e., employing a perfusate at a defined pressure and directly measuring GFR during cold storage has never been used due to various encumbering factors such as reabsorption, e.g., of water, sodium and potassium and the consequent energy loss. Such consequences do not permit measurement of GFR as a direct function of kidney viability.

It is suggested in the art that assays to determine the functional viability of preserved organs should allow the surgeon to determine if an organ will be functionally viable when it is transplanted via noninvasive, nondestructive means. According to one researcher, no such assay exists (Southard et al. *Cryobiology*, 26:232-238, 1989). Essentially, the prior art suggests that a need exists to develop a reliable viability assay so that nonviable kidneys are never transplanted (D'Alessandro et al. "Organ Preservation In: *Horizons in Organ Transplant Action*, 74:1083-1095, 1994).

Increasing the number of organs for transplant therapy by increasing the number of voluntary donors has not been successful. Further complicating the situation is an increase in the incidence of renal disease in the United States and other countries around the world (Booster et al. *Transpl. Proc.*, 25(1):1503-1504, 1993). An increase in organ procurement may depend on increasing recovery of available but higher risk donors and organs.

Xenografts, organs from other species, represent the potentially largest pool of donor tissue. Xenograft survival problems are critical and, therefore, are not a potential organ source in the near future (Lloveras et al. *Transpl. Proc.*, 25(6):3169-3170, 1993). Patients who have sustained cardiac standstill (non-heartbeating) have become a major focus of organ procurement. However, the need for additional precaution in preservation of organs and intraoperative procedures are required for this patient population (Rowinski et al. *Transpl. Proc.*, 25(1):1511-1512, 1993).

Therefore, a means for monitoring kidney functionality during cold storage in a manner which would provide an easy and direct assessment of kidney function remains a critical need. The present invention o provides such a methodology which employs a conventional perfusate with reduced glomerular impermeable colloid concentration utilized at a perfusion pressure which can surprisingly avoid tubular reabsorption and consequent energy loss. Such method permits direct and continuous assessment of kidney functionality by measuring GFR by simple and convenient means.

The present invention utilizes the direct measurement of Glomerular Filtration Rate (GFR) through measurement of urine formation during the perfusion period to continuously assess the functional state of the kidney. The present invention further contemplates assessment of afferent arteriole and efferent arteriole vascular patency and the maintenance of tubular patency as well as integrity of tubule cells during perfusion. This invention also provides a method for monitoring cold ischemia damage as an indication for timing and dosage of nephrotoxic immunosuppressant agents, e.g., Cyclosporin A. The present invention also provides a therapeutic method for maintaining tubule patency and a device for performing the tests of the present invention.

SUMMARY OF THE INVENTION

One innovation of the present invention resides in the finding that by manipulating the concentration of colloid in the standard UW solution in relation to perfusion pressure, glomerular filtration occurs in a manner which totally avoids reabsorption by the kidney tubules. The advantage provided by this discovery relative to the prior art is that GFR can be used as a direct measure of the functional viability of the kidney in the absence of other considerations. Previously, GFR could not be used as a direct measure of kidney functional viability during perfusion as a consequence of reabsorption of fluid by the tubules resulting from inadequate perfusates and improper perfusion pressures.

More specifically, in accordance with the present invention it has been determined that measuring Glomerular Filtration Rate and Total Flow at a constant perfusion pressure permits: (1) a determination of overall kidney functionality; (2) a determination of afferent and efferent arteriole constriction; (3) correlations of functional parameters such as GFR, TF and FF with baseline data to permit the assessment of the donor kidney for transplant; (4) an evaluation of appropriate dosages of nephrotoxic immunosuppressant agents and timing for immunosuppressant administration. The present invention also provides a therapeutic method for ensuring the patency of the tubules.

The present invention is directed to a method for monitoring and assessing functional viability of a donor kidney comprising direct continuous measurement of glomerular filtration rate (GFR) during cold perfusion of the donor kidney employing a perfusion solution comprising a glomerular impermeable colloid at concentrations ranging from about 0.1 g % to about 4.0 g % as correlated with a range of perfusion pressure of about 5 mmHg to about 60 mmHg. From these parameters a ratio can be calculated. Generally, a ratio of about 1 g % to about 10 mmHg can be used by the skilled artisan to establish appropriate colloid-pressure parameters. Below a perfusate colloid concentration of 1 g %, however, it is preferred to employ a minimum of about 5 mmHg to about 10 mmHg of perfusion pressure. Specifically, between a colloid concentration of 0.1 g % to about 1 g % of the perfusate the perfusion pressure is preferred to be between about 5 mmHg and about 10 mmHg to affect best results. These conditions permit perfusion of the tubules without causing reabsorption and consequent utilization of metabolic resources as previously observed.

Continuous measurement of GFR is readily determined as a direct function of urine output.

Still another aspect of this invention is directed to continuous monitoring of TF and calculation of FF as a fraction of GFR and TF, i.e., GFR/TF.

The present invention is also directed to in vitro methods of: assessing kidney functional viability and arteriolar status; correlating various kidney physiologic parameters, i.e., GFR, TF and FF in the determination of viability; and evaluating appropriate dosing and timing regimens for administering nephrotoxic immunosuppressant agents. These methods comprise continuous perfusion of the kidney at a conventional cold perfusion temperature of about 7° to about 10° C. employing a perfusate having a reduced glomerular impermeable colloid concentration correlated with a particular perfusion pressure to avoid tubular reabsorption; monitoring the rate and volume of urine produced by the kidney; directly measuring changes in GFR by plotting changes in urine output; and monitoring total flow.

The present invention permits continuous assessment of kidney functional viability by correlating increases in GFR, at constant TF, evidencing relative functional viability, and decreases in GFR, at constant TF, evidencing functional deterioration.

The present invention also permits assessment of efferent arteriolar status by calculating filtration fraction and correlating FF spikes, relative increases in GFR and decreases in TF, with the presence of efferent arteriole constriction.

The present invention also permits assessment of afferent arteriolar status by calculating filtration fraction and correlating a relative decrease in GFR, a decrease in TF and the absence of a FF spike, with the presence of afferent arteriole constriction.

The present invention also permits assessment of afferent and efferent arteriolar constriction by correlating a disproportionate decrease in GFR, a decrease in TF and the absence of a FF spike, with the presence of afferent and efferent arteriole constriction.

A further aspect of the present invention permits the correlation of various kidney physiologic parameters GFR, TF and FF to generate data relating to the general functional viability of a kidney comprising direct and continuous measurement of GFR, continuous monitoring of TF and calculations of FF.

A still further aspect of the present invention is directed to a method for evaluating appropriate dosing and timing regimens for administering nephrotoxic immunosuppressant agents comprising correlating lowered GFR with cold ischemia damage and the resultant need to delay administration of nephrotoxic immunosuppressants.

Another aspect of the present invention is directed to a therapeutic method for ensuring the patency of the kidney tubules comprising continuous perfusion of the kidney at a conventional cold perfusion temperature of about 7° to about 10° C. comprising a perfusate having a selected glomerular impermeable colloid concentration and essential tubule nutrients balanced with a particular perfusion pressure wherein tubule occlusion is prevented by the absence of tubule reabsorption.

Yet another aspect of the present invention is directed to a collection device for positioning the ureter of a donor kidney during continuous cold perfusion, the device permits segregation of urine which may conveniently be collected and measured by an automatic siphon allowing for visual quantitation of urine output.

DETAILED DESCRIPTION OF THE INVENTION

Figure 1A:
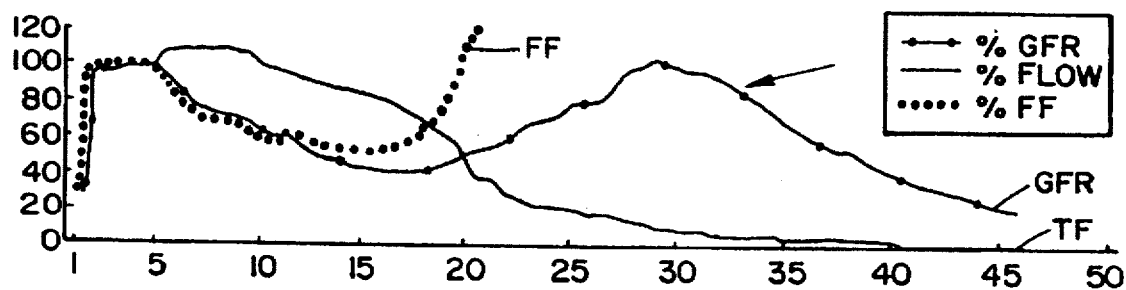
FIGS. 1a–1c show kidneys that have been cold perfused stored over approximately 24–48 hours. Total flow (TF), glomerular filtration rat (GFR) and filtration fraction (FF) are all plotted. The arrow in 1a indicates a large increment in GFR resulting from an increased efferent constriction. The arrows in 1b and 1c indicate no increment in GFR.

The present invention provides a method for assessing the functional viability of a donor kidney by monitoring one or more of certain kidney-specific physiologic markers. In particular, the present invention provides a method for ascertaining kidney function by measuring Glomerular Filtration Rate (GFR) during cold perfusion of a donor kidney employing a perfusion solution having a particular colloid concentration. Perfusion is conducted at a selected perfusion pressure which is correlated with the concentration of the colloid of the perfusate in a manner which avoids reabsorption by the kidney tubules.

It has been surprisingly discovered in accordance with the present invention that the concentration of the colloid of the perfusate and the perfusion pressure can be correlated in a ratio in such a manner as to totally avoid tubule reabsorption of e.g. water, sodium and potassium by the kidney tubules during cold perfusion, thereby permitting direct assessment of the relative kidney functionality by measurement of GFR or GFR and TF. Such measurements permit determinations of the relative functional viability of the donor kidney for transplantation. These parameters can be determined in order to further assess arteriolar status, tubule patency and appropriate dosing and timing regimens for administering nephrotoxic immunosuppressant agents post transplant.

The present invention also permits continuous monitoring of two additional parameters Total Flow (TF) and Filtration Fraction (FF). By Total Flow is meant the total fluid flow through the kidneys. The Total Flow is generally quantitated in µl/min in rodents and in ml/min in humans. Total Flow is determined by the additive resistances of the afferent and efferent arterioles. TF can influence glomerular pressure but does not determine glomerular pressure per se. The filtration fraction (FF) is the fraction of the kidney fluid flow that becomes glomerular filtrate. Thus the filtration fraction can be described as the ratio of GFR to TF i.e., FF=GFR/TF. By continuously measuring GFR and TF it is now possible in accordance with the present invention to assess the status of the kidney vasculature.

By functional viability is meant the physiological changes in the ability of the kidney to filter during cold storage at about 7° to about 10° C. over the period of time from harvest of the organ to transplantation.

The perfusion solution of the present invention is a modified Belzer-MPS™ solution the formulation of which comprises Sodium Gluconate, Potassium Phosphate, Monobasic NF, Magnesium Gluconate, USP (dihydrate), Glucose, Beta D(+), Adenine (free base), Ribose (D-), HEPES (free acid), Glutathione (reduced form), Calcium Chloride, USP (dihydrate), Mannitol, USP, Modified Hydroxyethyl Starch (3.75 g %), Sodium Hydroxide (pH 7.4) and Water. In use, the skilled artisan may augment the solution with conventional additives such as Insulin, Dexamethasone and Penicillin.

By Glomerular Filtration Rate (GFR) is meant the rate at which fluid is filtered through the kidney. GFR is the art established "Gold Standard" measurement of kidney function. More specifically, GFR means the quantity of filtrate formed by the kidney. GFR is also directly related to the pressure in the glomerulus. Glomerular pressure is determined by the relative resistances between the afferent and efferent arterioles. The afferent arteriole serves as the pathway by which fluid enters the glomerulus. The efferent arteriole is the pathway by which fluid leaves the glomerulus.

The arterioles form an important part of the kidney vasculature and the assessment of their respective functional and physiological condition is extremely advantageous to the overall determination of kidney viability. The kidney vasculature supplies needed nutrients to the surrounding tissue and plays a unique function in forming an ultrafiltrate of plasma (glomerular filtration). The tubule component of the kidney is functionally interrelated with the vascular component. Once fluid is filtered through the glomerulus it enters the tubule. The tubule component generally serves to reabsorb fluids.

Previous studies attempting to evaluate tubular activity in cold stored kidneys reported substantial tubular reabsorption, energy utilization and obstruction. (Gianello et al. supra.) These studies utilized albumin-based perfusates. Thus, prior researchers found that perfusion of the tubules would necessarily result in substantial tubular reabsorption, cellular sloughing and energy utilization. Tubular reabsorption, cellular sloughing and energy utilization impeded prior efforts to directly assess kidney viability because the tubules would either be clogged with dead cells or the tubules would be actively reabsorbing fluid.

The present invention employs the above-identified composition or its equivalent, a glomerular impermeable colloid based perfusate at a concentration of about 0.1 g % to about 4.0 g %, a perfusion pressure range of about 5 mmHg to about 60 mmHg and a temperature of about 7° to about 10° C. From these parameters a ratio can be calculated. Generally, a ratio of about 1 g % to about 10 mmHg can be used by the skilled artisan to establish appropriate colloid-pressure parameters. Below a perfusate colloid concentration of 1 g %, however, it is preferred to employ a minimum of about 5 mmHg to about 10 mmHg of perfusion pressure. Specifically, between a colloid concentration of 0.1 g % to about 1 g % of the perfusate the perfusion pressure is preferred to be between about 5 mmHg and about 10 mmHg to affect best results. These conditions permit perfusion of the tubules without causing reabsorption and consequent utilization of metabolic resources as previously observed.

By glomerular impermeable colloid is meant a component of a perfusate (e.g. modified hydroxyethyl starch or albumin) which characteristically stabilizes the glomerular membrane throughout a perfusion period.

A preferred glomerular impermeable colloid based perfusate employs modified hydroxyethyl starch at the concentration, pressures and temperatures identified above.

In accordance with the present invention, a biphasic response in filtration (GFR) has been observed which can be utilized in the assessment and determination of kidney viability. This phenomenon has generally been observed during the first ten hours of cold storage by continuous monitoring of the mammalian kidneys by the method of the present invention. The biphasic response is characterized by an initial increase in filtration (GFR) as determined by measuring changes in urine output per unit of time. The increase in filtration is followed by a steady state at which filtration and total flow are about the same. The steady state is then followed by a decrease in filtration as determined by measuring changes in urine output per unit of time.

The rate at which increases or decreases in GFR occur serves as a direct indicator of kidney functionality. Specifically a steep rate of decline in GFR measured per unit of time is indicative of a deteriorating kidney. A rate of incline in GFR measured per unit time is indicative of a functionally viable kidney. A steady GFR (no slope) in conjunction with a steady Total Flow indicates that GFR has plateaued and the kidney is functionally relatively viable (but less so than in the inclining state). A steady GFR or one declining with a small slope relative to unit time, especially with no appreciable Total Flow, indicates that the kidney has deteriorated and is not transplantable.

Thus, another embodiment of the present invention is directed to measuring the rate of increase or decrease in filtration, i.e. the GFR biphasic response, during cold perfusion in accordance with the present method to determine the relative viability of the kidney.

In accordance with the present invention a donor kidney is harvested and cold perfused as soon as practicable employing a perfusate comprising from about 0.1 g % to about 4.0 g % Modified Hydroxyethyl Starch at a pressure of from about 5 mmHg to about 60 mmHg (as determined by the conventional ratio between colloid concentration and perfusion pressure) and a temperature from about 7° to about 10° C. For example, a conventional in-line probe can be used to monitor perfusion pressure and total flow. The donor kidney is placed in a conventional cold perfusion cassette, which is removably attached to a conventional recirculating perfusion pump (such as the Waters MOX-100DCM cassette perfusion pump), the renal artery is removably connected to a tube in the cassette, which is removably connected to the perfusion pump. The renal vein is not attached to the perfusion apparatus and remains free to drain. The ureter is positioned on an inclined trough or other collection device provided within the perfusion cassette, thus permitting gravitational urine flow from the kidney. The inclined trough is removably attached to an automatic siphon, for example, in the perfusion cassette. The perfusate is pumped into the renal artery and urine exits the kidney through the ureter, while other fluid exits the kidney through the renal vein. Renal vein fluid is recirculated through the perfusion apparatus, while urine is collected with the aid of an automatic siphon, a drop counter or a volumetric chamber. Urine volume and urine flow rate are conveniently measured continuously in µl or ml increments depending on the kidney species. Urine output is then correlated directly with GFR. Increasing GFR per unit of time correlates generally with kidney functional viability, while decreasing GFR per unit of time correlates generally with kidney deterioration and no GFR correlates with a non-viable kidney.

In accordance with the present invention the ureter may be placed on an inclined trough which is removably attached to an automatic siphon within the perfusion cassette which permits urine output to be measured directly during monitoring.

In accordance with the present invention GFR may be measured employing an art recognized balance combined with a computer software program to instantaneously and continuously measure perfusion pressure and total flow in milliliter or microliter increments of urine output in weight per unit time depending on the species of kidney.

The present invention permits GFR to be measured by conventional means known to the skilled artisan including visual counting of urine drops formed and more preferably with a volumetric chamber or an automatic siphon.

Utilizing the methodology of the present invention, the inventor has unexpectedly discovered that a sequence of changes in afferent and efferent arteriole resistance occur during cold storage monitoring. When FF spike (steeply sloped FF) is observed it generally indicates that the relationship between GFR and TF has changed due to a proportionately greater GFR. This can occur when efferent resistance preferentially increases causing glomerular capillary pressure to rise. This situation will cause an increase in filtration (GFR) and a decrease in TF. The inventor has discovered that this manifestation is characteristic of efferent arteriole constriction. Similarly, a relative decrease in GFR with a concomitant decrease in TF and the absence of a FF spike indicates afferent arteriole constriction. In addition, a disproportionate decrease in GFR with a concomitant decrease in TF and the absence of a FF spike suggests concurrent efferent and afferent arteriole constriction. Each of the three foregoing results provide useful information for the practitioner wishing to administer appropriate vasodilators or vasoconstrictors post-transplantation as well as in the assessment of the relative viability of the kidney.

In a still further embodiment, the inventors have discovered that the present methodology can assist practitioners in deciding the timing and dosing of initial post-transplant Cyclosporin A immunosuppression. By continuously monitoring filtration (GFR) from harvest to transplant, a decreasing GFR immediately prior to transplant signals an ischemically damaged organ, which should not receive nephrotoxic immunosuppression e.g. Cyclosporin A. Ischemia is known to enhance the nephrotoxicity of Cyclosporin A. Thus postponing immunosuppressant therapy until GFR is steadily increasing, as determined by conventional in vivo tests, may aid overall graft survival.

In accordance with the present invention the inventor has now discovered that tubular perfusion is beneficial and can be used to perform the same functions as vascular perfusion by maintaining lumen (tubule) patency while providing valuable nutrients. Furthermore, tubular obstruction, which is a common result of tubule ischemic damage, may be minimized by tubular perfusion. Absent any reabsorption in the tubules, the inventor has, for the first time recognized that the rate at which the fluid, e.g., urine, leaves the kidney is identical to the rate at which it was filtered through the glomerulus, i.e., GFR. The recognition that urine output and GFR can be equated provides the skilled artisan with a novel and simple diagnostic tool which can be used to continuously assess kidney function.

EXAMPLE 1

Physiologic Marker Monitoring

Figure 1B:
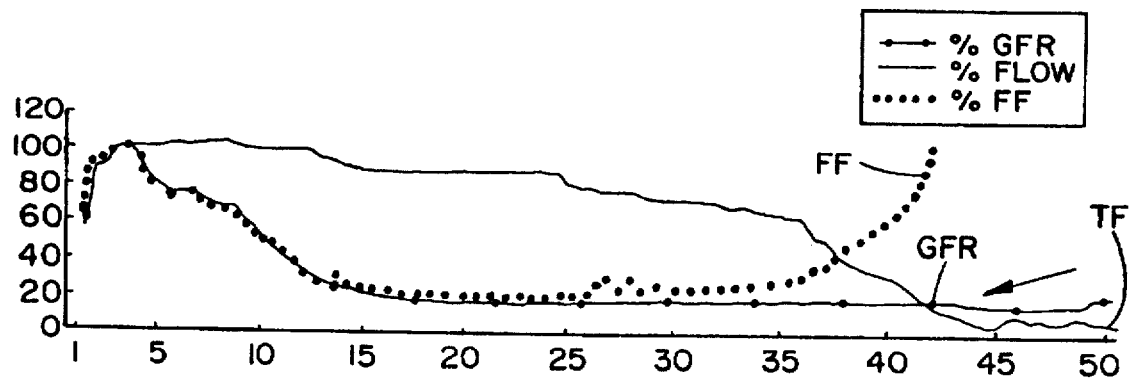
Figure 1C:
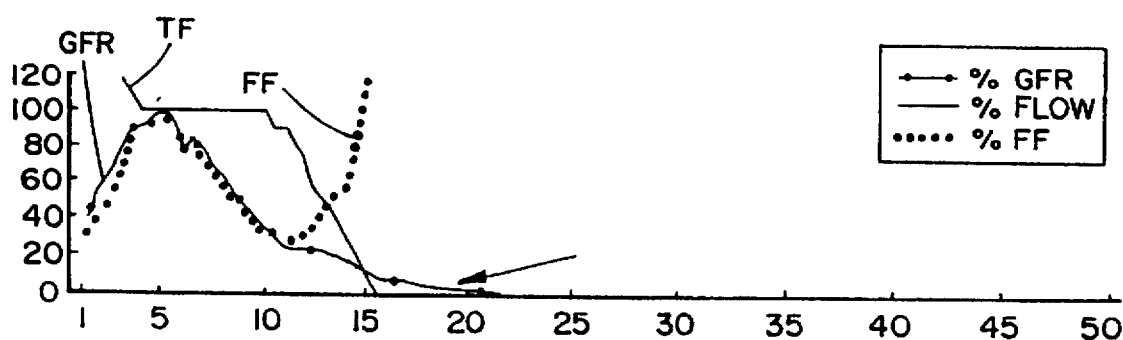
Figure 2:
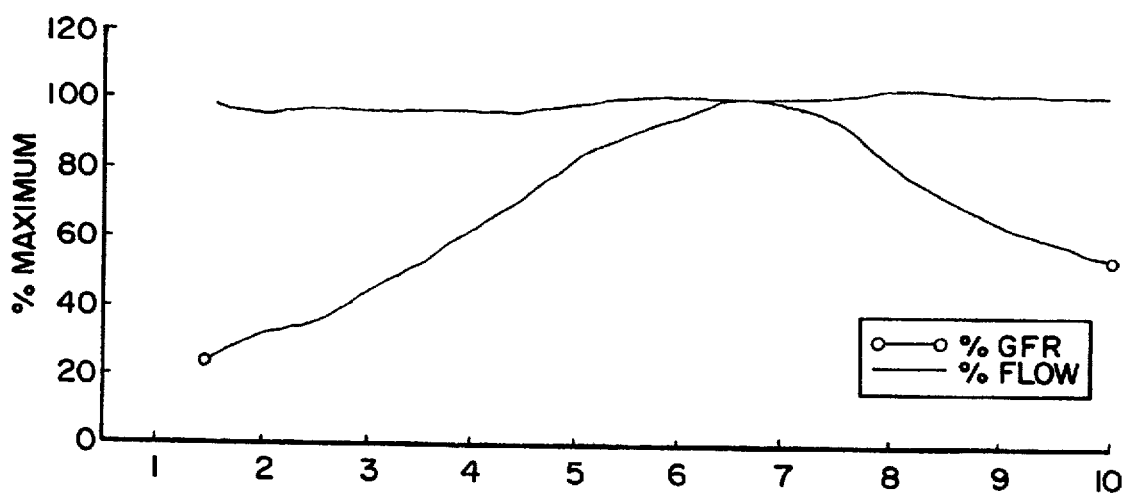
FIG. 2 shows a biphasic response in filtration during the first ten hours of cold storage. GFR, TF and FF are all 100% at the time when the biphasic GFR response is at its maximum.
Figure 3:
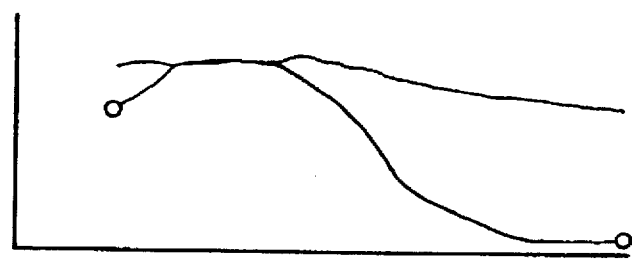
FIGS. 3–10 represent independent experiments demonstrating the biphasic response in filtration during the first ten hours of cold storage.
Figure 4:
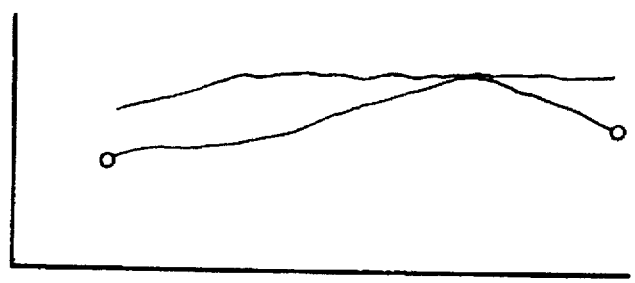
Figure 5:
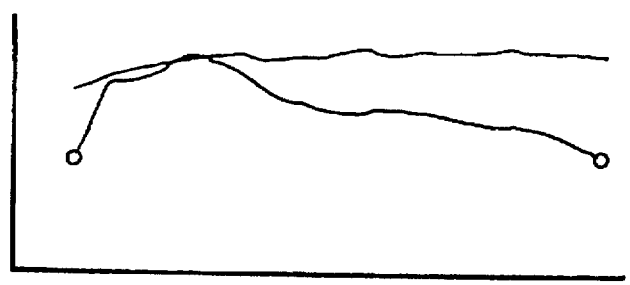
Figure 6:
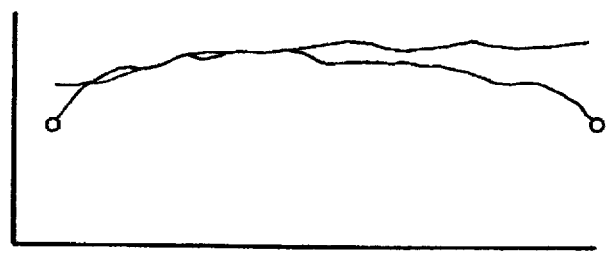
Figure 7:
Figure 8:
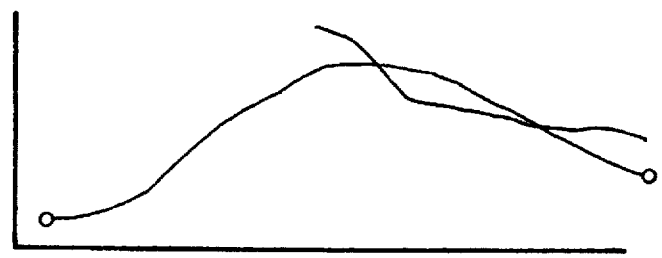
Figure 9:
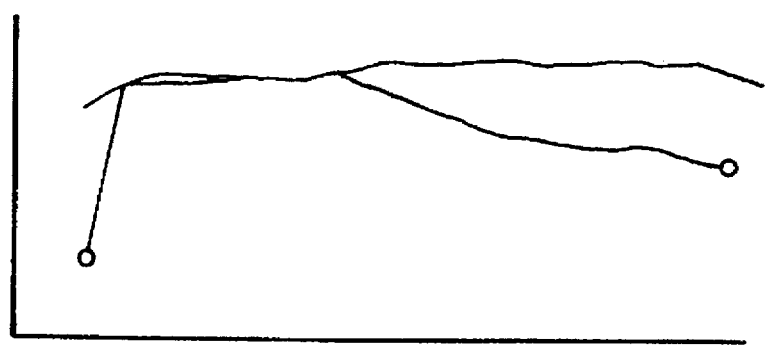
Figure 10:

Lewis rat kidneys (N=20) were cold perfused at 7° C. to 10° C. and continuously monitored for up to 72 hours to examine the range of cold storage responses (see FIGS. 1a–1c). During cold storage, TF decreased over time. Efferent arteriole resistance (constriction of the efferent arteriole, as measured by relative increases in GFR and decreases in Total Flow) increased during cold storage monitoring causing glomerular capillary pressure to rise. The increase in glomerular capillary pressure caused a relative increase in filtration (GFR) and a decrease in total flow and marked spike in filtration fraction (FF) (see FIG. 1a). The decrease in TF and relative increase in GFR caused the spike in the FF.

Efferent constriction accompanied by afferent constriction resulted in a dramatic increase in FF. This increase was likely due to a drop in TF, rather than an increase in GFR. (See FIGS. 1b and 1c). The drop in TF caused an increase in the GFR/TF ratio and thus increased FF. The increase in FF may occur at different times and may be a marker of kidney viability as shown in FIGS. 1a–1c.

In FIG. 1b, FF dramatically increased at approximately 40 hours post-harvest in vitro but in FIG. 1c, the spike in FF occurred at approximately 15 hours post-harvest in vitro. The FF spike appears to be an indicator of irreversible renal tissue deterioration and a useful marker for maximum cold storage time.

These results indicated that cold storage monitoring can inferentially differentiate kidney arteriolar status during cold storage.

EXAMPLE 2

Predictive Utility of Biphasic GFR

Continuous monitoring of the kidney post-harvest in vitro uncovered a biphasic response in filtration during the first ten hours of storage (FIGS. 2–10). The "GFR maximum" (see FIGS. 2–10), occurred at different times within the first ten hours following harvest (i.e., in vitro time=X axis). The Y axis (% maximum) is a percentage of an actual value determined by choosing, as a reference point, ("GFR maximum"), the time at which GFR reached a maximum in the first 10 hours of cold storage. Thus, GFR, TF and FF are all standardized to 100% at the time when the GFR is at its maximum. This standardization allowed for more efficient comparisons of kidney values as shown in FIGS. 2–10.

Specifically, GFR increased an average of 34.1% (p<0.002) from 2 hours to "GFR maximum" and dropped an average of 49.2% (p<0.001) from "GFR maximum" to 10 hours. Statistical significance was evaluated using a post-hoc ANOVA comparison of means using repeated measures and the Newman-Kuels test.

Neither the initial increase in filtration nor the decrease that followed required a change in total organ flow (TF). TF at 2 hours, "GFR maximum", and 10 hours, was not significantly different and averaged 4533±250 µl/min, 4650±380 µl/min, and 4083±460 µl/min respectively.

Data from the biphasic GFR response demonstrated marked clinical implications. Knowledge of the biphasic GFR response reflects the length of time a donor kidney can be cold stored without significant damage. It has been reported that cadaveric kidneys transplanted in less than 6 hours, or living non-related donor kidney transplants (LNR), have similar outcomes as living related transplants (LR) (Teraski et al., *Transplants*, Los Angeles, Calif., UCLA Tissue Typing Laboratory, 1991). Since cadaveric kidneys are usually transplanted after several hours of cold storage and have historically poorer graft outcomes than LR transplants, knowledge that a decrease in filtration following the GFR peak correlates to a loss in post-transplant function provides a useful indicator of graft success.

EXAMPLE 3

Kidney Harvest, Perfusion Storage and Transplant

A starch based perfusate (Belzar MPS™ Perfusate, modified starch concentration 3.75 g %), was used in twenty genetically matched Lewis rats (275–300 g) (Harland Sprague-Dawley, Indianapolis, Ind.). Kidneys were initially cold perfused in vivo at 7°–10° C., through a distal aortic catheter. Cold perfusate was pumped through the kidneys at physiologic pressures while simultaneously clamping the aortas above the kidneys.

Only left kidneys were harvested immediately following aortic clamping. The renal artery, vein and ureter were catheterized during cold perfusion. The renal vein catheter had to be large (0.07"ID, 0.11"OD) to accommodate low pressure venous flow. The kidney and all three catheters were stabilized on a small platform in a kidney transplant cassette.

Immediately, following harvest, each kidney was tested to insure proper kidney and catheter patency by cold perfusing the renal artery at 60 mmHg and measuring the total kidney flow (TF). A TF of 3.6 ml/min–4.2 ml/min was required to insure uniform resistance in all kidneys.

The kidney cassette was then connected to a perfusion apparatus and pump (Baxter Rotary Dialysis Pump, Chicago, Ill.) using universal silastic fittings on the renal artery and vein. This system mimicked the in vivo vasculature of the rat kidney by recirculating cold perfusate at approximately 450 mls/min. The system does not force fluid through the kidney but allowed the actual kidney resistance, at any given moment, to determine flow. The system therefore permitted the arterioles to react to pressure changes naturally.

A catheter coming from the main recirculating line (from the pump) was connected to the kidney module, thus mimicking the way the renal artery comes off the aorta in vivo. Since, kidney flow out of the recirculating line was less (1–10 ml/min) than the total flow being recirculated (approximately 450 ml/min), changes in kidney flow did not significantly change pressure in the recirculating line. This system allowed kidney flow to increase or decrease as a result of kidney resistance without altering central pressure generated from the main recirculating line.

Total flow and GFR were monitored. An in-line probe (Transonic FM #T106, Ithaca, N.Y.) was used to measure TF. A 27 gauge needle was inserted into the renal artery silastic catheter to monitor perfusion pressure (Stathum Strain Gauge, Gould Windograf #40-8474, Valley View, Ohio). The ureter catheter (0.02"ID) was extended and placed in a beaker under oil inside a Mettler PM100 balance. The Mettler balance permitted accurate measurements of microliter increments of urine. Instantaneous microliter GFR changes in a cold perfused kidney were monitored (i.e., in weight per unit time) by combining the Mettler balance with a Mettler computer software program (Balancelink, Mettler). The Mettler balance and accompanying software permitted continuous 2 day GFR monitoring of rat kidneys.

The perfusion pump, kidney cassette and recirculating tubing were placed in a 7°–10° C. cold room to maintain tissue temperature during monitoring.

Transplantation was accomplished by matching the male universal fittings on the renal artery and vein to the female fittings on the aorta and vena cava extending from the abdomen of the recipient Lewis rat. The transplanted kidney was insulated with Saran Wrap™ and maintained at body temperature 37° C.

Utilizing a standard in vivo iohexal measurement of urine flow rate, the transplanted kidneys retained an average of 87% of their overall function as compared to the untouched kidney in the genetically matched recipient rat when transplanted within two hours post-harvest. The urine concentration of iohexal multiplied by the urine volume divided by the plasma concentration of iohexal (0.1 mg/ml) provided a measurement GFR. The transplanted kidney GFR divided by the GFR of the untouched kidney multiplied by 100 provides a measurement of relative kidney function achieved by the transplanted kidney.

EXAMPLE 4

A human kidney is cold (7° C. to 10° C.) perfused in vivo at physiological pressure without cessation of heart beat. A starch based perfusate (Belzar MPS™ Perfusate, modified colloid concentration 0.1 g %–4 g %), is employed throughout the perfusion period.

The kidney is harvested as soon as practicable, while continually perfusing the aorta. The renal artery is catheterized, as soon as practicable, and the renal artery is attached to a Waters MOX-100DCM Perfusion Apparatus, taking care to avoid air embolisms during transfer to the perfusion apparatus. The renal vein is left free so that fluid from the renal vein flows freely into the perfusion apparatus. The ureter is positioned in an inclined trough thereby permitting gravity induced fluid flow therefrom. The trough supporting the ureter is attached to an automatic siphon capable of collecting 10 ml urine. The kidney is stabilized on an inclined platform in the perfusion apparatus and is not handled again until transplant.

The kidney is initially perfused at a pressure of 45 mmHg to ensure proper kidney patency by measuring TF.

Cold perfusate is recirculated through the kidney at approximately 200 ml/min. The system does not force fluid through the kidney but allows the actual kidney resistance, at any given moment, to determine flow. The system therefore permits the arterioles to react to pressure changes naturally.

A catheter coming from the main recirculating line, (through the pump) is connected to the kidney, thus mimicking the way the renal artery comes off the aorta in vivo. Since, kidney flow out of the recirculating line is less, i.e., about 80 ml/min than the total flow being recirculated (about 200 ml/min), changes in kidney flow will not significantly change pressure in the recirculating line. This system allows kidney flow to increase or decrease as a result of kidney resistance without altering central pressure generated from the main recirculating line.

Total flow, GFR and perfusion pressure are continuously monitored by conventional systems resident in the perfusion apparatus and determinations respecting kidney functional viability are made. Instantaneous and continuous milliliter GFR changes in a cold perfused kidney are monitored conventionally by measuring how the rate at which the automatic siphon empties. The automatic siphon will permit continuous 2 day GFR monitoring of urine output.

The perfusion pump, kidney cassette and recirculating tubing are placed in a 7°–10° C. cold room to maintain tissue temperature during monitoring.

Transplantation of the monitored kidney will greatly improve graft success rates, diminish hospital stays, eliminate the need for further dialysis and prolong the useful life of the kidney in the recipient.

What is claimed:

1. A method for monitoring and determining the functional viability of a donor kidney prior to transplantation comprising:

continuously, vascularly perfusing said kidney at about 7° to about 10° C. with a perfusate comprising a glomerular impermeable colloid, wherein the concentration of the colloid is about 0.1 to 4 gram percent of the perfusate, wherein kidney resistance determines the flow rate, wherein the perfusion pressure is no lower than 5 mmHg and the perfusion pressure is further correlated to the colloid concentration in a ratio of about 1 gram percent per 10 mmHg which prevents kidney tubule reabsorption of water and permits glomerular filtration of said perfusate and, determining the glomerular filtration rate of said kidney, which is equal to the urine output rate wherein an increase in the glomerular filtration rate is indicative of functional viability an a decrease in a glomerular filtration rate is indicative of functional deterioration.

2. The method of claim 1 which further comprises measuring the total flow rate of said perfusate through the kidney.

3. The method of claim 2 wherein a constant glomerular filtration rate in conjunction with a constant total flow rate which is measured at the maximum glomerular filtration rate is indicative of functional viability.

4. The method of claim 2 wherein a constant glomerular filtration rate in conjunction with a total flow rate which approaches zero is indicative of functional deterioration.

5. The method of claim 2 which further comprises calculating the filtration fraction ratio by dividing the glomerular filtration rate by the total flow rate.

6. The method of claim 5 wherein an increase in the glomerular filtration rate in conjunction with a decrease in total flow rate and a resulting filtration fraction ratio spike is indicative of efferent arteriole constriction.

7. The method of claim 5 wherein a decrease in the total flow rate in conjunction with the absence of a filtration fraction ratio spike is indicative of afferent arteriole constriction.

8. A method for preserving the functional viability of a donor kidney tubule prior to transplantation comprising:

continuously, vascularly perfusing said kidney at about 7° to about 10° C. with a perfusate comprising a glomerular impermeable colloid wherein the concentration of the colloid is about 0.1 to 4 gram percent of the perfusate, wherein kidney resistance determines the flow rate, wherein the perfusion pressure is no lower than 5 mmHg and the perfusion pressure is further correlated to the colloid concentration in a ratio of about 1, gram percent per 10 mmHg, which prevents kidney tubule reabsorption of water and permits glomerular filtration of said perfusate.

* * * * *